(12) United States Patent
Marin et al.

(10) Patent No.: US 7,094,938 B1
(45) Date of Patent: Aug. 22, 2006

(54) PROCESS FOR THE PREPARATION OF SUBSTITUTED FLUORENES

(75) Inventors: Vladimir Marin, Houston, TX (US); Abbas Razavi, Mons (BE)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 11/133,855

(22) Filed: May 20, 2005

(51) Int. Cl.
*C07C 13/465* (2006.01)
*B01J 31/00* (2006.01)
*C07F 17/00* (2006.01)
*C08F 4/44* (2006.01)

(52) U.S. Cl. ..................................................... 585/27
(58) Field of Classification Search .................... 585/27
See application file for complete search history.

(56) References Cited

U.S. PATENT DOCUMENTS 6,939,928 B1  9/2005  Kawai et al.

OTHER PUBLICATIONS

Kajigaeshi et al., Bull. Chem. Soc. Jpn., vol. 59, No. 1, pp. 97-103 (1986).*

* cited by examiner

Primary Examiner—Porfirio Nazario-Gonzalez
(74) Attorney, Agent, or Firm—Diane L. Kilpatrick-Lee

(57) ABSTRACT

Methods for the preparation of fluorenyl-type ligand structures and substituted fluorenyl groups which may be employed in metallocene-type olefin polymerization catalysts. There is provided a 2,2'-dihalogen-diphenylmethylene having a methylene bridge connecting a pair of phenyl groups. Each phenyl group has a halogen on a proximal carbon atom relative to the methylene bridge. The halogenated diphenylmethylene is reacted with a coupling agent comprising a Group 2 or 12 transition metal in the presence of a nickel or palladium-based catalyst to remove the halogen atoms from the phenyl groups and couple the phenyl groups at the proximal carbon atoms to produce a fluorene ligand structure. The coupling agent may be zinc, cadmium or magnesium and the catalyst may be a monophosphene nickel complex. The halogenated diphenylmethylene may be an unsubstituted ligand structure or a monosubstituted or disubstituted ligand structure. The halogenated diphenylmethylene may be monosubstituted with a tertiary butyl group or may be a dialkyl diphenylmethylene having alkyl substituents at the directly distal positions of the phenyl groups relative to the methylene bridge.

17 Claims, No Drawings

PROCESS FOR THE PREPARATION OF SUBSTITUTED FLUORENES

FIELD OF THE INVENTION

This invention relates to fluorenyl-type ligands useful in metallocene-type olefin polymerization catalysts and more particularly, to the preparation of such fluorenyl-type ligand structures.

BACKGROUND OF THE INVENTION

Fluorenyl based metallocene catalysts are effective catalysts in the polymerization, including homopolymerization or copolymerization of olefin polymers such as ethylene, propylene and higher olefins or other ethylenically unsaturated monomers.

Fluorenyl-type metallocenes are characteristically in the form of metallocene ligand structures characterized by bridged cyclopentadienyl and fluorenyl groups. An example is isopropylidene (cyclopentadienyl)(fluorenyl) zirconium dichloride. The cyclopentadienyl group or the fluorenyl group can be modified by the inclusion of substituent groups in the cyclopentadienyl ring or the fluorenyl group which modifies the structure of the catalyst and ultimately the characteristics of the polymers produced. Thus, olefin polymers such as polyethylene, polypropylene, which may be atactic or stereospecific such as isotactic or syndiotactic, and ethylene-higher alpha olefin copolymers such as ethylene propylene copolymers, can be produced under various polymerization conditions and employing various polymerization catalysts.

The metallocene catalyst based upon a bridged cyclopentadienylfluorenyl ligand structure can be produced by the reaction of 6,6-dimethyl fulvene, which may be substituted or unsubstituted, with a fluorene, which in turn may be substituted or unsubstituted, to produce the bridged isopropylidene cyclopentadienylfluorenyl ligand structure. This ligand is, in turn, reacted with a transition metal halide such as zirconium tetrachloride to produce the bridged zirconium dichloride.

Fluorenyl ligands may be characterized by the following numbering scheme for the fluorenyl ligand as indicated in Formula (1):

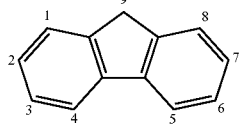
(1)

In this numbering scheme, 9 indicates the bridgehead carbon atom. The remaining carbon atoms available to accept substituents are indicated by numbers 1–4, one phenyl group of the ligand, and numbers 5–8 of the other phenyl group of the fluorenyl ligand.

Alpha olefin homopolymers or copolymers may be produced using metallocene catalysts under various conditions in polymerization reactors which may be batch type reactors or continuous reactors. Continuous polymerization reactors typically take the form of loop-type reactors in which the monomer stream is continuously introduced and a polymer product is continuously withdrawn. For example, polymers such as polypropylene, polyethylene or ethylene-propylene copolymers involve the introduction of the monomer stream into the continuous loop-type reactor along with an appropriate catalyst system to produce the desired olefin homopolymer or copolymer. The resulting polymer is withdrawn from the loop-type reactor in the form of a "fluff" which is then processed to produce the polymer as a raw material in particulate form as pellets or granules. In the case of $C_{3+}$ alpha olefins, such as propylene, or substituted ethylenically unsaturated monomers such as styrene or vinyl chloride, the resulting polymer product may be characterized in terms of stereoregularity, for example, isotactic polypropylene or syndiotactic polypropylene.

The structure of isotactic polypropylene can be described as one having the methyl groups attached to the tertiary carbon atoms of successive monomeric units falling on the same side of a hypothetical plane through the main chain of the polymer, e.g., the methyl groups are all above or below the plane. Using the Fischer projection formula, the stereochemical sequence of isotactic polypropylene is described as follows:

(2)

In Formula (2), each vertical segment indicates a methyl group on the same side of the polymer backbone. Another way of describing the structure is through the use of NMR. Bovey's NMR nomenclature for an isotactic pentad as shown above is . . . mmmm . . . with each "m" representing a "meso" dyad, or successive pairs of methyl groups on the same said of the plane of the polymer chain. As is known in the art, any deviation or inversion in the structure of the chain lowers the degree of isotacticity and crystallinity of the polymer.

In contrast to the isotactic structure, syndiotactic propylene polymers are those in which the methyl groups attached to the tertiary carbon atoms of successive monomeric units in the chain lie on alternate sides of the plane of the polymer. Syndiotactic polypropylene using the Fisher projection formula can be indicated by racemic dyads with the syndiotactic pentad rrrr as shown by Formula (3):

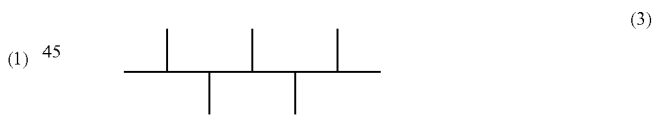
(3)

In Formula (3), the vertical segments indicate methyl groups in the case of syndiotactic polypropylene, or other terminal groups, e.g. chloride, in the case of syndiotactic polyvinyl chloride, or phenyl groups in the case of syndiotactic polystyrene.

Other unsaturated hydrocarbons which can be polymerized or copolymerized with relatively short chain alpha olefins, such as ethylene and propylene include dienes, such as 1,3-butadiene or 1,4-hexadiene or acetylenically unsaturated compounds, such as methylacetylene.

Procedures for the synthesis of substituted fluorenes used to produce metallocene polymerization catalysts are influenced by specific features of the fluorene ligand. The direct electrophilic substitutions of fluorene occur predominantly at the 2- or 2,7-positions having the highest electron density. For example, 2,7-di-t-butylfluorene can be prepared from the reaction of fluorene with t-butyl chloride in the presence of $AlCl_3$:

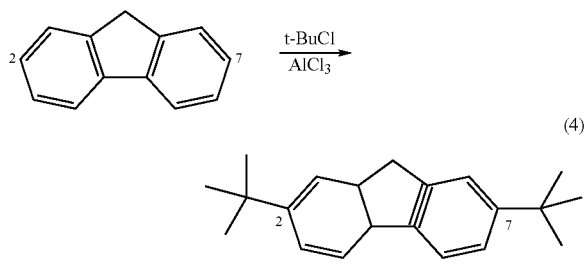

(4)

As another example, as disclosed in EP1138687, 3,6-di-t-butyl fluorene can be prepared by the reaction of 2,2'-diiodo-4,4'-di-t-butyldiphenylmethane with copper as shown in the following reaction:

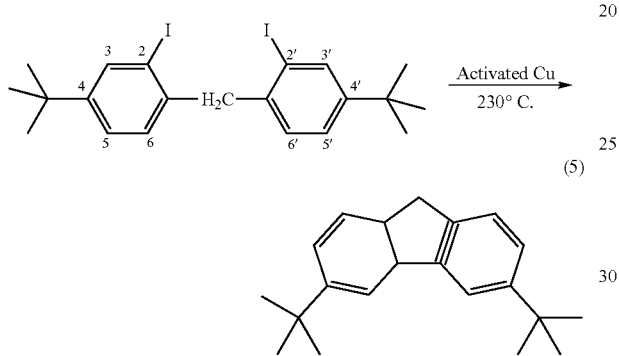

(5)

This reaction, which occurs at a high temperature (230–250° C.), results in a mixture of products. When using this method, several purification steps are needed in order to obtain the pure 3,6-di-tert-butyl-fluorene.

SUMMARY OF THE INVENTION

In accordance with the present invention, there are provided methods for the preparation of fluorenyl-type ligand structures and substituted fluorenyl groups which may be employed in metallocene-type olefin polymerization catalysts. In carrying out the present invention, there is provided a 2,2'-dihalogen-diphenylmethylene having a methylene bridge connecting a pair of phenyl groups. Each of the phenyl groups has a halogen on a proximal carbon atom relative to the methylene bridge. The halogenated diphenylmethylene is reacted with a coupling agent comprising a transition metal selected from Groups 2 or 12 of the Periodic Table of Elements. This reaction is carried out in the presence of a nickel or palladium-based catalyst to remove the halogen atoms from the phenyl groups and couple the phenyl groups at the proximal carbon atoms to produce a fluorene ligand structure. In a preferred embodiment of the invention, the coupling agent is selected from the group consisting of zinc, cadmium and magnesium and more specifically, zinc. The catalyst may be a monophosphine nickel complex characterized by the formula:

$NiX_2(PR_3)$ (6)

or a diphosphine nickel complex characterized by the formula:

$NiX_2[PR_2-CH_2)_n-PR_2]$ (7)

wherein X is a halogen, n is a number within the range of 1–10 and R is an alkyl, aryl or cyclic group.

The halogenated diphenylmethylene may be an unsubstituted ligand structure or a monosubstituted or disubstituted ligand structure. In one embodiment of the invention, the halogenated diphenylmethylene is monosubstituted with an alkyl group, an alicyclic group or an aryl group having from 1 to 20 carbon atoms. In a preferred embodiment of the invention, the halogenated diphenylmethylene is monosubstituted with a tertiary butyl group.

In a further embodiment of the invention, the halogenated diphenylmethylene is a dialkyl diphenylmethylene having alkyl substituents at the directly distal positions of the phenyl groups relative to the methylene bridge. In this embodiment of the invention, the product produced by the coupling reaction is a 3,6-dialkyl fluorene. Preferably, each of the alkyl substituents is an isopropyl or higher group, having a molecular weight of at least 43. More preferably, the alkyl substituents are tertiary butyl groups.

In a more specific aspect of the invention, the halogenated diphenylmethylene is a substituted diphenyl methylene characterized by the formula:

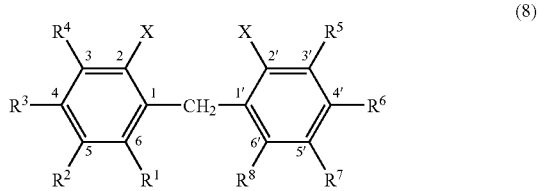

(8)

In Formula (8), X is a halogen atom. Each of $R^1$–$R^8$ is a hydrogen atom, an aryl group or an alkyl group, which may be the same or different, provided that no more than 3 of the $R^1$–$R^4$ groups or no more than 3 of the $R^5$–$R^8$ groups are hydrogen atoms. Thus, the substituted diphenylmethylene characterized by Formula (8) is at least a disubstituted ligand structure.

In a preferred embodiment of the invention, $R^1$, $R^4$, $R^5$ and $R^8$ are hydrogen and $R^2$, $R^3$, $R^6$ and $R^7$ are alkyl groups. In one embodiment of the invention, $R^3$ and $R^6$ are tertiary butyl groups and $R^2$ and $R^7$ are $C_1$–$C_{20}$ alkyl groups. In another embodiment of the invention, $R^3$ and $R^6$ are tertiary butyl groups and $R^1$, $R^2$, $R^4$, $R^5$, $R^7$ and $R^8$ are hydrogen atoms.

In a preferred embodiment of the invention, the reaction with the coupling agent is carried out at a temperature of less than 100° C. Preferably, the coupling reaction is carried out at temperatures within the range of 20–80° C. for a time period within the range of 2–3 hours.

Further embodiments of the present invention involve the preparation of substituted fluorenes employing fluorenes or substituted fluorenes as starting materials. In one embodiment of the invention, there is provided a 3,6-disubstituted fluorene characterized by the formula:

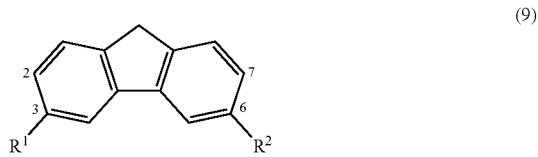

(9)

In Formula (9), $R^1$ and $R^2$ are $C_1$–$C_{20}$ alkyl groups which may be the same or different.

The disubstituted fluorene is reacted with a brominating agent to produce 2,7-dibromo-3,6-disubstituted fluorene characterized by the formula:

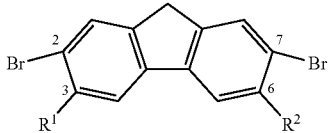
(10)

wherein $R^1$ and $R^2$ are as defined above.

The 2,7-dibromo-3,6-disubstituted fluorene is reacted with a magnesium or zinc-based Grignard reagent characterized by the formula:

RMX (11)

wherein R is a $C_1$–$C_{20}$ alkyl or a $C_6$–$C_{20}$ alicyclic or aryl group, M is magnesium or zinc, and X is a halogen.

The product of this reaction is a 2,7,3,6-tetrasubstituted fluorene characterized by the formula:

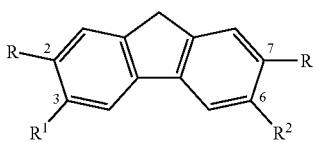
(12)

Alternatively, the 2,7-dibromo-3,6-disubstituted fluorene characterized by Formula (10) is reacted in the presence of a palladium-based catalyst with an arylboronic acid characterized by the formula:

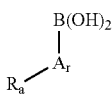
(13)

wherein $A_r$ is a phenyl or a naphthyl group which may be substituted or unsubstituted and $R_a$ is a $C_1$–$C_{20}$ alkyl group.

The result of this reaction is a 2,3,6,7-substituted fluorene characterized by the formula:

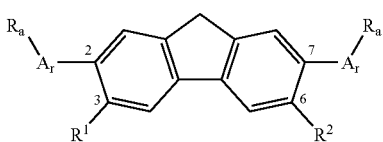
(14)

In a preferred embodiment of the invention, $A_r$ is a phenyl group and $R^1$ and $R^2$ are tertiary butyl groups.

In a further aspect of the invention, a 3,6-disubstituted fluorene characterized by Formula (9) above is reacted with a chloromethylating agent to produce a 2(7)-monochloromethylene-3,6-disubstituted fluorene, a 2,7-dichloromethylene-3,6-disubstututed fluorene or a 2,4,7-trichloromethylene-3,6-disubstituted fluorene characterized by Formulas (15) through (17), respectively.

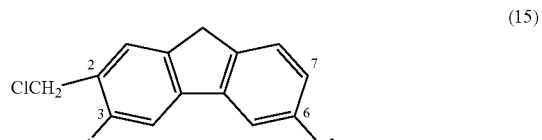
(15)

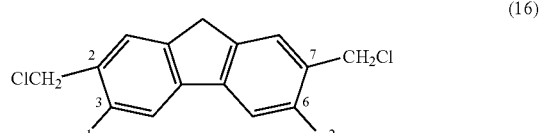
(16)

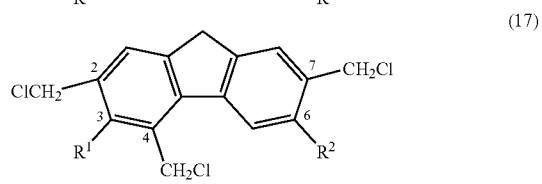
(17)

The chloromethylene disubstituted fluorene characterized by the above Formulas (15)–(17) is reacted with a reducing agent to produce the corresponding monomethyl, dimethyl or trimethyl-disubstituted fluorene as characterized by Formulas (18), (19) or (20), respectively.

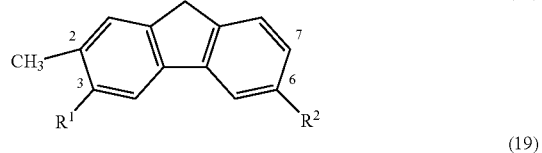
(18)

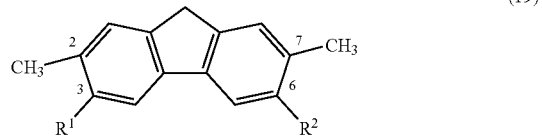
(19)

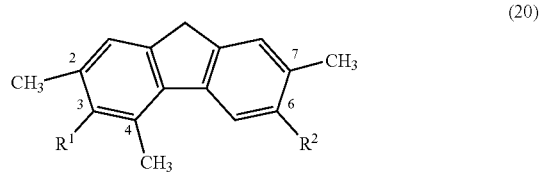
(20)

Preferably, the groups $R^1$ and $R^2$ are tertiary butyl groups.

Yet a further embodiment of the invention employs as a starting material a 2,7-disubstituted fluorene characterized by the formula:

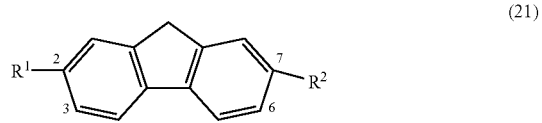
(21)

wherein $R^1$ and $R^2$ are $C_1$–$C_{20}$ alkyl or alicyclic groups which may be the same or different. The disubstituted fluorenyl group is reacted with a brominating agent to produce a 4-bromo-3,6-disubstituted fluorene characterized by the formula:

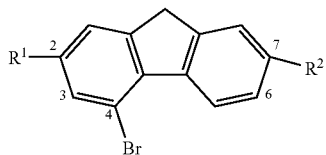
(22)

The 4-bromo-3,6-disubstituted fluorene is reacted in the presence of a nickel or palladium catalyst with a magnesium or zinc-based Grignard reagent as characterized by Formula (11) above to produce a 2,4,7-substituted fluorene characterized by the formula:

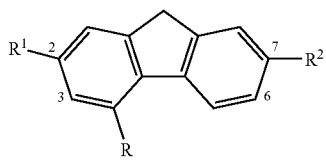
(23)

Alternatively, the 4-bromo-3,6-disubstituted fluorene is reacted in the presence of a palladium-based catalyst with an arylboronic acid characterized by Formula (13) above to produce a 2,4,7-substituted fluorene characterized by the formula:

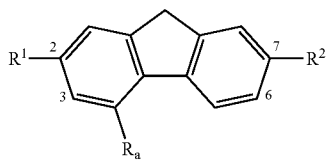
(24)

In a preferred embodiment of the invention, $R^1$ and $R^2$ are tertiary butyl groups.

In yet a further aspect of the invention, fluorene is reacted with a tertiary butylating agent to produce a 2,7-ditertiary-butyl fluorene which is reacted with a brominating agent to produce a 4-bromo-2,7-ditertiarybutyl fluorene characterized by the formula:

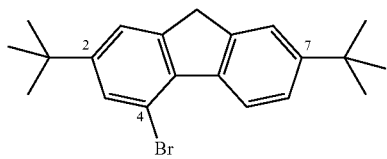
(25)

This brominated fluorene is reacted with aluminum chloride and benzene to dealkylate the fluorene ligand to produce a 4-bromo fluorene characterized by the formula:

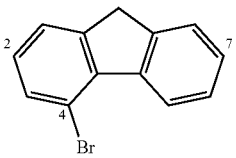
(26)

This 4-bromo fluorene ligand is reacted in the presence of a nickel or palladium-based catalyst with a magnesium or zinc Grignard reagent as characterized by Formula (11) above or with an arylboronic acid as characterized by Formula (13) above to produce a 4-substituted fluorene characterized by the formula:

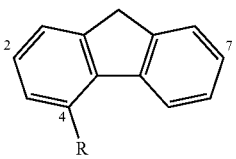
(27)

DETAILED DESCRIPTION OF THE INVENTION

In accordance with the present invention, provided are methods for the preparation of fluorenyl-type ligand structures by a protocol which employs readily available reactants and provides a fluorenyl ligand in high yields, in contrast to the use of a copper agent as described previously. The process of the present invention can be carried out under moderate temperature conditions and is not attended by laborious and time consuming purification procedures.

As noted previously, in a typical numbering scheme applied to fluorenyl groups, the central carbon atom (the bridgehead carbon atom) extending between the phenylene groups, is numbered 9 and the carbon atoms of the phenylene groups are numbered 1–8. In the diphenylmethylene group from which the fluorenyl group may be derived, the carbon atoms in one phenyl group are numbered 1–6 and the counterpart carbon atoms of the other phenyl group are numbered 1'–6'. These numbering schemes are shown in the following reaction illustrating the reaction of a halogenated diphenylmethylene with a coupling agent to produce a corresponding fluorenyl ligand.

(28)

This reaction indicates the basic reaction employed in the present invention in which the 2,2-dihalogen diphenylmethylene is reacted with a zinc, cadmium or magnesium coupling agent over a nickel or palladium-based catalyst. In Reaction (28), X is a halogen, preferably chlorine, bromine or iodine, and more preferably, iodine. In Reaction (28), the carbon atom in the methylene bridge of the diphenylmethylene corresponds to the bridgehead carbon atom 9 of the fluorenyl group. The carbon atoms 3, 4, 5 and 6 correspond respectively to carbon atoms 4, 3, 2 and 1 of the fluorenyl group and the carbon atoms 3', 4', 5' and 6' correspond respectively to carbon atoms 8, 7, 6 and 5 of the fluorenyl group. In the case where the fluorenyl group is only monosubstituted, it will be recognized that 2-substitution is equivalent to 7-substitution, 3-substitution is equivalent to 6-substitution and so on.

The foregoing reaction is carried out in the presence of nickel(II) catalysts, preferably phosphine nickel(II) complexes, specifically, $Ni[(PPh_3)_2]Cl_2$, $[Ph_2PC_2H_4PPh_2]NiCl_2$ and $[Ph_2PC_3H_6PPh_2]NiCl_2$ or palladium (0) catalyst, preferably $Pd(PPh_3)_4$. Preferably, at least 0.5 mol. %, and more preferably 0.5–2.0 mol. %, of catalyst is employed. According to a preferred embodiment of the invention, the process is carried out in the presence of a polar solvent, such as tetrahydrofuran (THF) or N,N-dimethylformamide. The reaction is preferably carried out at a temperature within the range of 20–80° C., for a period of 1–48 hours, and more preferably for 2–3 hours.

Examples of reaction routes which may be employed in carrying out the invention are as follows, with

indicating a methyl group and indicating a tertiary butyl group.

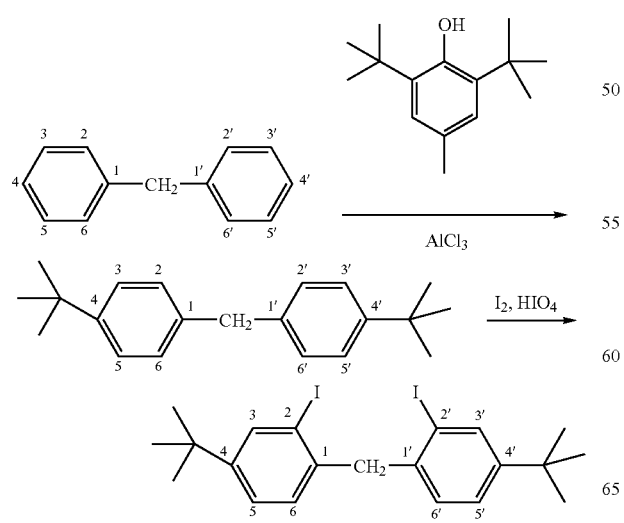

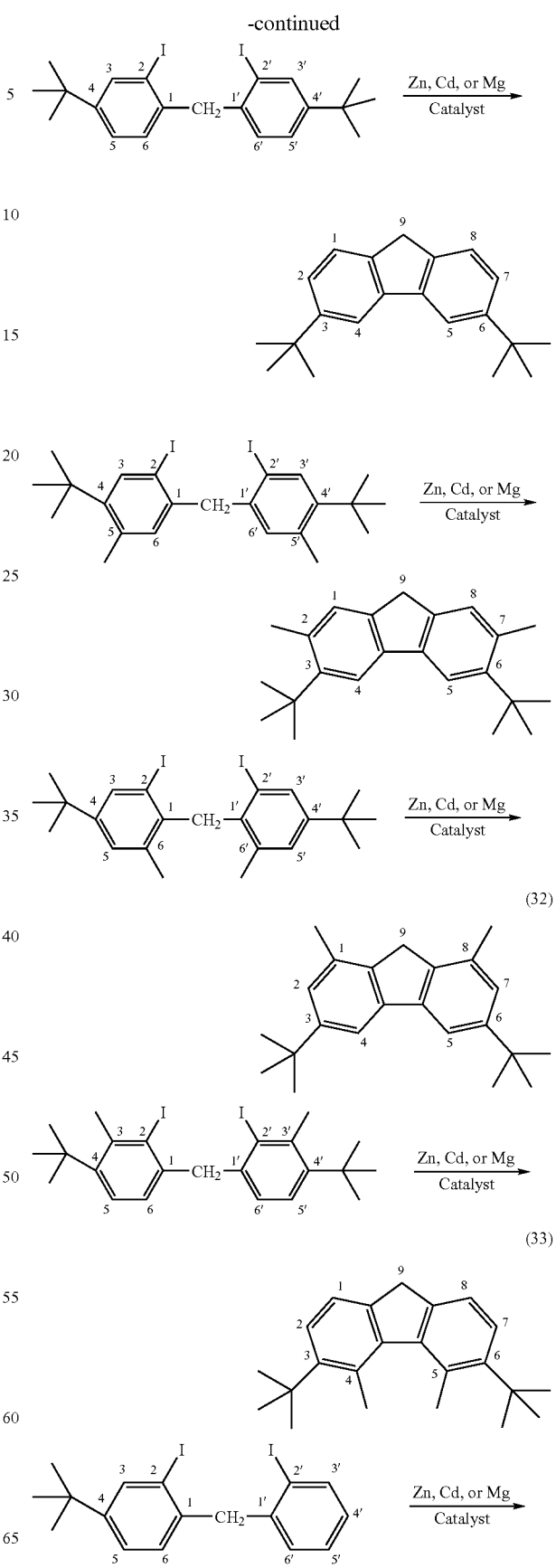

-continued

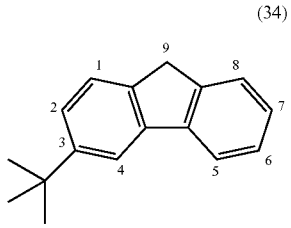
(34)

The reaction involves the use of a brominating reagent and a Grignard reagent or an arylboronic acid as described previously. The term "Grignard reagent" as used herein, is meant to denote a conventional Grignard reagent characterized by the formula:

RMgX (35)

and also the zinc equivalent in which the magnesium atom is replaced with a zinc atom to provide the reagent:

RZnX (36)

X is a halogen, typically chlorine or bromine.

Another reaction route can be used to make tetra-substituted fluorenes. This procedure includes reacting a 3,6-substituted fluorene having the same or different substituent groups with at least 2 equivalents and preferably 2.0–2.2 equivalents of a brominating agent, preferably N-bromosuccinimide in propylene oxide at 60–80° C. for 2–6 hours to produce a 2,7-dibromo-3,6-disubstituted fluorene as follows:

(37)

The 2,7-dibromo-3,6-disubstituted fluorene is reacted with a Grignard compound RMgX or RZnX in the presence of a nickel or palladium-based catalyst to produce a 2,3,6,7-susbstituted fluorene:

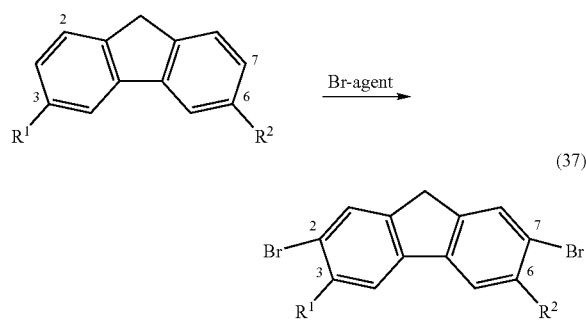
(38)

Alternatively, the 2,7-dibromo-3,6-disubstituted fluorene is reacted with an arylboronic acid as depicted by Formula (13) in which the aryl group may be phenyl, substituted phenyl, naphthyl or substituted naphthyl, in the presence of a palladium-based catalyst to produce 2,3,6,7-susbstituted fluorene as exemplified by the following reaction:

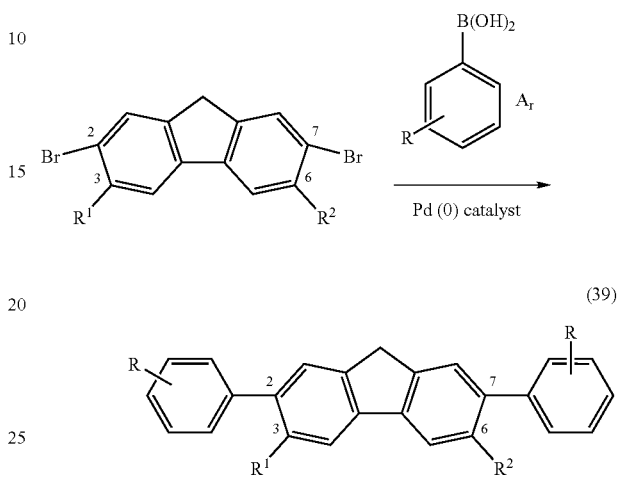

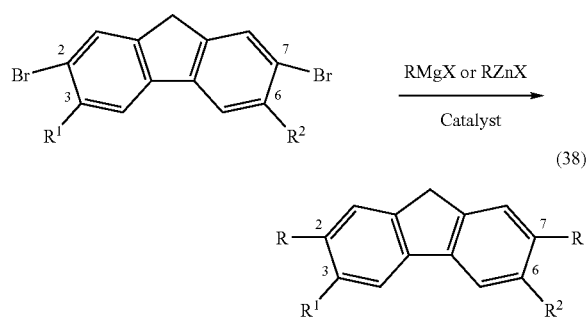
(39)

The first procedure comprises reacting the 2,7-dibromo-3,6-disubstituted fluorene with at least 2 equivalents and preferably 2–7 equivalents of the Grignard reagent, magnesium or zinc-organic compound. This reaction is carried out in the presence of a nickel or palladium catalyst, preferably Ni[(PPh$_3$)$_2$]Cl$_2$, [Ph$_2$PC$_2$H$_4$PPh$_2$]NiCl$_2$, [Ph$_2$PC$_3$H$_6$PPh$_2$]NiCl$_2$ or Pd(PPh$_3$)$_4$, with at least 0.5 mol. %, and preferably 0.5–2.0 mol. % of catalyst. The reaction procedure is preferably carried out in the presence of a polar solvent such as diethyl ether or THF. The reaction is preferably carried out at a temperature within the range of 20–60° C. for a time period of 1 hour to 5 days, and more preferably, for 2–24 hours.

The alternative procedure involves the reaction 2,7-dibromo-3,6-disubstituted fluorene with at least 2 equivalents and preferably 2–3 equivalents of the arylboronic acid. This reaction is carried out in the presence of a palladium catalyst, preferably Pd(PPh$_3$)$_4$, with at least 0.5 mol. %, and preferably 0.5–5.0 mol. % of palladium catalyst, and in the presence of at least 3 equivalents of Na$_2$CO$_3$ or K$_2$CO$_3$, preferably 3–7 equivalents of Na$_2$CO$_3$ or K$_2$CO$_3$. Preferably, the alternative reaction procedure is carried out in the presence of toluene, alcohol and water at ratios of 10:(1–2):(1–0.1), respectively. The reaction is preferably carried out at a temperature ranging from 20–150° C. for a period of 1–24 hours, and more preferably, 2–3 hours. The resulting fluorene product can be purified by any suitable procedure such as by crystallization or by column chromatography.

Another reaction route which can be used to make tri-, tetra- and penta-substituted fluorenes includes reacting a 3,6-substituted fluorene having same or different groups with an chloromethylation agent to produce a 2(7)-monochloromethylene-3,6-disubstituted fluorene, 2,7-dichloromethylene-3,6-disubstituted fluorene, and 2,4,7-trichloromethylene-3,6-disubstituted fluorene in accordance with the following reactions:

(40)
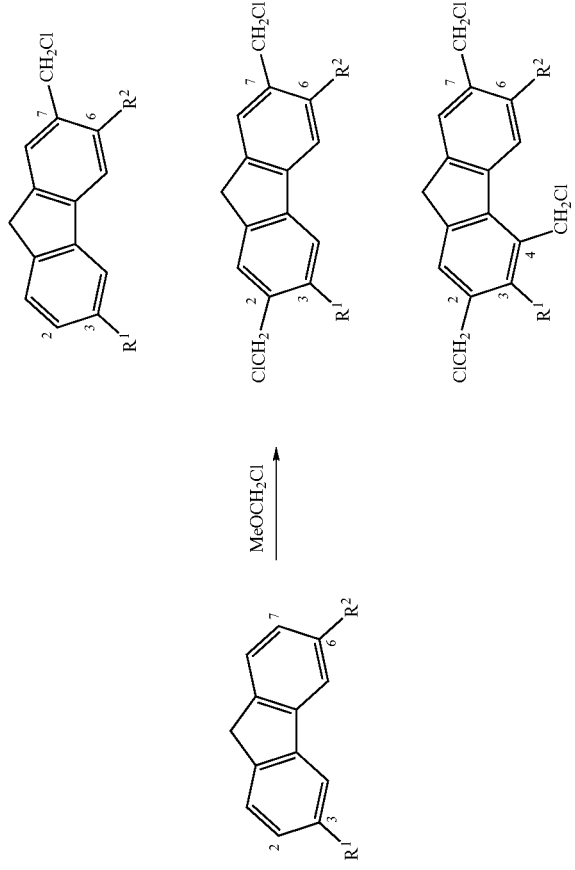

The chloromethylene fluorene derivatives are reacted with a reduction agent to produce the corresponding tri-, tetra- and penta-substituted fluorenes as follows:

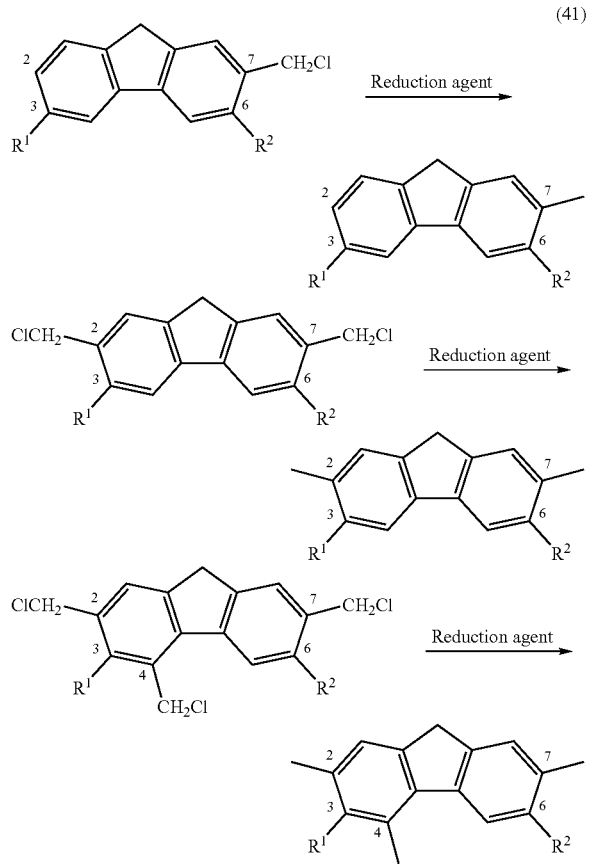

The reaction of 3,6-disubstituted fluorene producing the monochloromethylene derivative is carried out with at least 1 equivalent and preferably 1–2 equivalents of chloromethyl methyl ether to produce the 2(7)-monochloromethylene-3,6-disubstituted fluorene. This reaction is carried out in the presence of at least 1 mol. % and preferably 5–30 mol. % of $MCl_4$ (M=Ti, Zr, Hf) or $MCl_2$ (M=Zn, Cd), preferably $TiCl_4$ or $ZnCl_2$. The reaction is carried out at a temperature within the range of 0–40° C., preferably 0–10° C. for a period of 1–72 hours, and more preferably for 1–5 hours.

The 2,7-dichloromethylene-3,6-disubstituted fluorene is produced under similar condition using at least 2 equivalents and preferably 2–7 equivalents of chloromethyl methyl ether, 10–30 mol. % of $MCl_4$ (M=Ti, Zr, Hf) or $MCl_2$ (M=Zn, Cd), preferably $TiCl_4$ or $ZnCl_2$, at a temperature within the range of 0–40° C., preferably 20° C., for a period of 3–72 hours, and more preferably for about 24 hours. The 2,4,7-trichloromethylene-3,6-disubstituted fluorene is produced under conditions involving at least 3 equivalents and preferably 5–7 equivalents of chloromethyl methyl ether, 10–30 mol. % of $MCl_4$ (M=Ti, Zr, Hf) or $MCl_2$ (M=Zn, Cd), preferably $TiCl_4$ or $ZnCl_2$, at a temperature within the range of 0–40° C., preferably 20° C., for a period of 3–72 hours, and more preferably for about 24 hours. The reactions are carried out in an organic solvent, preferable carbon disulfide or without solvent. The products are purified by crystallization from hot heptanes.

An alternate procedure involves reacting the chloromethylene derivatives with at least 0.5 equivalent and preferably 0.5–1.0 equivalent per each chloromethylene unit of $LiAlH_4$ in THF for 1–5 hours at 20–60° C. to produce the corresponding methyl-fluorenes.

Another process which can be used to make 2,4,7-substituted fluorenes involves the following procedure. A 2,7-substituted fluorene having the same or different substituent groups (alkyl or cyclic, $C_1$–$C_{20}$) is reacted with a bromination agent to produce a 4-bromo-2,7-disubstituted fluorene in accordance with the following reaction:

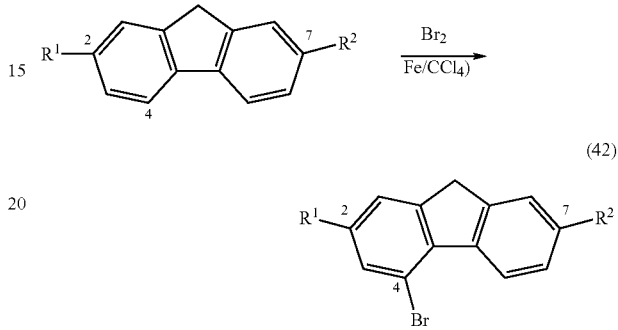

The 4-bromo-2,7-disubstituted fluorene is reacted with a Grignard reagent RMgX or RZnX (R=Alk, ($C_1$–$C_{20}$), Cyclic ($C_6$–$C_{20}$)) in the presence of a nickel or palladium-based catalyst to produce a 2,4,7-susbstituted fluorene in accordance with the following reaction:

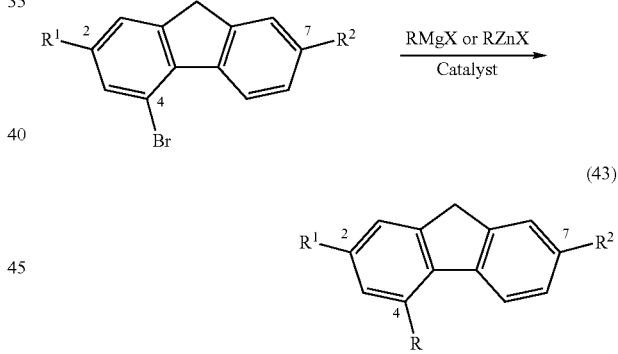

Alternatively, the 4-bromo-2,7-disubstituted fluorene is reacted in the presence of a palladium-based catalyst with an arylboronic acid in which the aryl group may be phenyl, substituted phenyl, naphthyl or substituted naphthyl, to produce 2,4,7-susbstituted fluorene as exemplified by the following reaction:

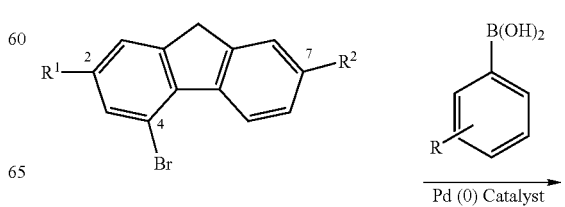

-continued

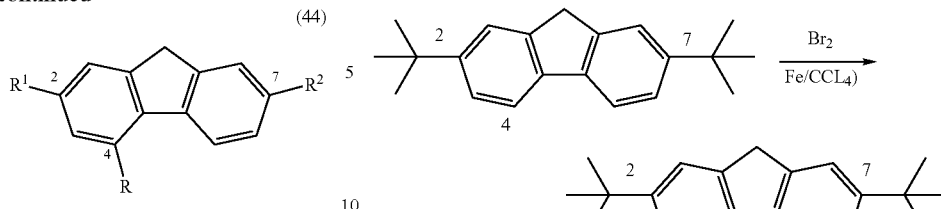

(44)

The initial reaction involving the 2,7-disubstituted fluorene is carried out with at least 1.0 equivalent and preferably 1.0–1.2 equivalents of bromine to produce the 4-bromo-2, 7-disubstituted fluorene. This reaction is carried out in the presence of iron powder in CCl$_4$ for 1–5 hours at 60–80° C.

The next reaction involves reacting 4-bromo-2,7-disubstituted fluorene with at least 1 equivalent and preferably 2–7 equivalents of the Grignard reagent magnesium or zinc-organic compounds. This reaction is carried out in the presence of a nickel or palladium-based catalyst, preferably Ni[(PPh$_3$)$_2$]Cl$_2$, [Ph$_2$PC$_2$H$_4$PPh$_2$]NiCl$_2$, [Ph$_2$PC$_3$H$_6$PPh$_2$] NiCl$_2$ or Pd(PPh$_3$)$_4$, with at least 0.5 mol. %, and preferably 0.5–2.0 mol. % of catalyst. In a preferred embodiment of the invention, the reaction is carried out in the presence of polar solvent, preferably in diethyl ether or THF. This reaction is preferably carried out at a temperature within the range of 20–60° C. for a period of 1 hour to 5 days, and more preferably for 2–24 hours.

The alternative reaction involves reacting the 4-bromo-2, 7-disubstituted fluorene with at least 1 equivalent and preferably 1.5 equivalents of the arylboronic acid. This reaction is carried out in the presence of a palladium-based catalyst, preferably Pd(PPh$_3$)$_4$, and with at least 0.5 mol. %, and preferably 0.5–5.0 mol. % of palladium catalyst, and in the presence of at least 3 equivalents of Na$_2$CO$_3$ or K$_2$CO$_3$. Preferably, the reaction involves 3–7 equivalents of Na$_2$CO$_3$ or K$_2$CO$_3$. In a preferred embodiment of the invention, this reaction is carried out in the presence of toluene, alcohol and water, preferably in ratios of 10:(1–2):(1–0.1), respectively. The initial reaction is preferably carried out at a temperature within the range of 20–150° C. for a period of 1–24 hours, and more preferably for a period of 2–3 hours. The resulting fluorene product is purified by crystallization or by column chromatography.

Another procedure for producing a 4-substituted fluorene involves the following reaction sequence. Fluorene is reacted with a tert-butylation agent to produce a 2,7-di-t-butyl-fluorene as follows:

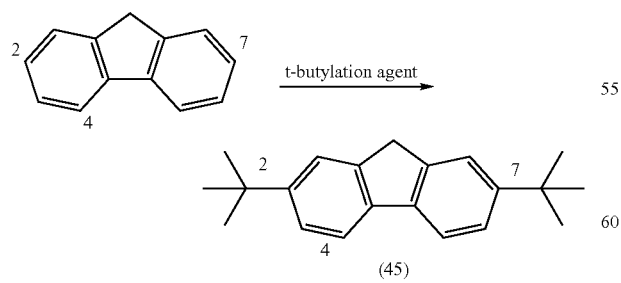

(45)

The 2,7-di-t-butyl-fluorene is reacted with a bromination agent to produce a 4-bromo-2,7-di-tbutyl-fluorene in accordance with the following reaction:

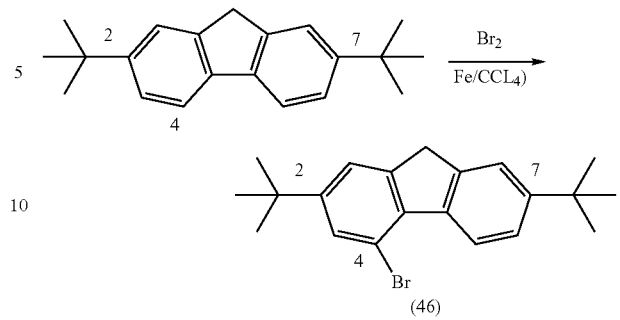

(46)

The 4-bromo-2,7-di-t-butyl-fluorene is then reacted with benzene and AlCl$_3$ to produce 4-bromo-fluorene as follows:

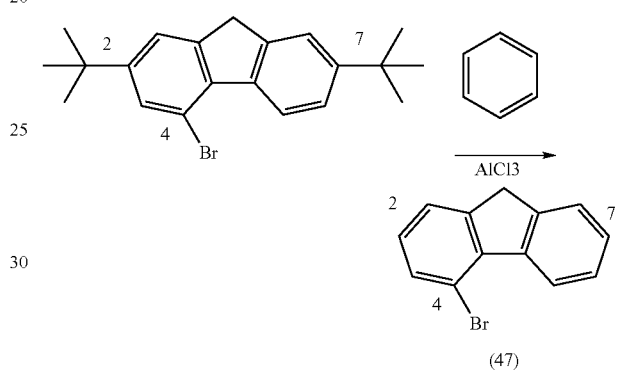

(47)

The 4-bromo-fluorene is reacted with a Grignard reagent RMgX or RZnX (R=Alk, (C$_1$–C$_{20}$), cyclic (C$_6$–C$_{20}$) as defined above in the presence of a nickel or palladium-based catalyst, or with an arylboronic acid in which the aryl group may be phenyl, substituted phenyl, naphthyl or substituted naphthyl, to produce 4-R-fluorene as exemplified by the following reaction:

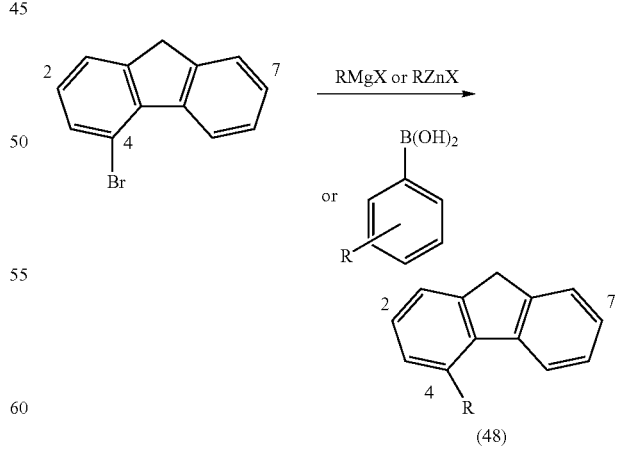

(48)

The reaction of fluorene with the tert-butylating agent involves the reaction of at least 1.0 equivalent of and preferably 1.0–1.2 equivalents of 2,6-di-t-butyl-p-cresol to provide a protection of the 2- and 7-positions of the fluorene.

This reaction can be carried out in the presence of AlCl₃ in nitromethane. The reaction of 2,7-di-t-butyl-fluorene with bromine is carried out under the conditions as described previously.

The next reaction is a deprotection reaction carried out with benzene in the presence of AlCl₃. The benzene functions as a solvent and a reactant. The reaction temperature ranges from 20–80° C., preferably 50° C. The reaction is carried out over a period of 0.5–5 hours, and preferably for 1–2 hours. The final reaction involves reacting 4-bromo-fluorene with the Grignard alkylation reagent or the aryloboronic acid under the conditions described above to produce the 4-substituted fluorene.

For a further description of the invention, reference is made to the following illustrative examples.

EXAMPLE 1

Synthesis of 3,6-di-tert-butyl-fluorene a) Synthesis of 4,4'-di-tert-butyldiphenylmethane To a solution of diphenylmethane (20.0 g, 0.119 mol) and 2,6-di-t-butyl-4-methylphenol (54.4 g, 0.238 mol) in nitromethane (300 ml) was added AlCl₃ (31.7 g, 0.238 mol) in nitromethane (100 ml) at 0° C. The reaction mixture was stirred for 120 min at 0° C. and then poured into ice water and extracted with ether (50 ml×2). The organic phase was washed with 10% NaOH (40 ml×5) and dried over MgSO₄. The solvents (nitromethane and ether) were evaporated using a rotary evaporator. The solid was washed with EtOH and dried. The yield was 17.1 g. ¹H NMR (CDCl₃): δ 7.31 (d, J=7.8 Hz, 4H, H$_{arom}$), 7.14 (d, J=7.8 Hz, 4H, H$_{arom}$), 4.06 (s, impurity), 3.93 (s, 2H, CH₂), 1.32 (s, 18H, t-Bu).

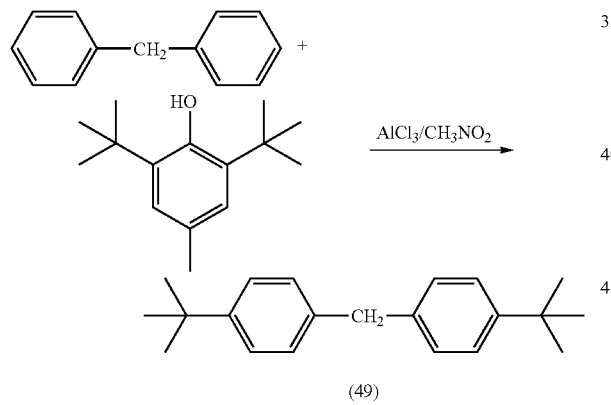

(49)

b) Synthesis of 2,2'-diiodo-4,4'-di-t-butyldiphenylmethane

To a solution of 4,4'-di-t-butyldiphenylmethane (9.17 g, 32.7 mmol), periodic acid dihydrate (4.47 g, 19.6 mmol) and iodine (8.30 g, 32.7 mmol) in glacial acetic acid (100 ml) was added H₂SO₄ (2 ml, 95%) and water (7 ml). The mixture was stirred at 85–90° C. for 20 hours and then poured into ice water and extracted with ether. The ether layer was washed with a NaHSO₃ solution, Na₂CO₃, followed by water and brine. The organic phase was dried over MgSO₄. The solvent was distilled off to obtain a yellow oil. The oil was chromatographed through Al₂O₃ to provide 15.3 g of product.

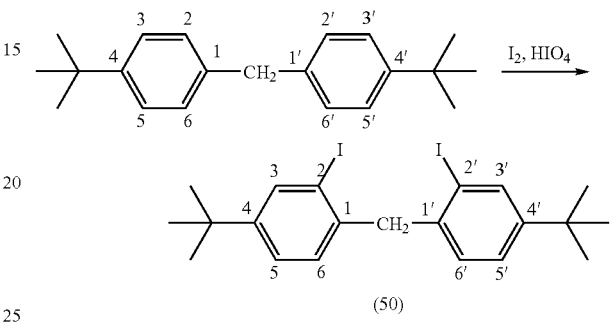

(50)

c) Coupling reaction of 2,2'-diiodo-4,4'-di-t-butyldiphenylmethane to produce 3,6-di-tert-butyl-fluorene

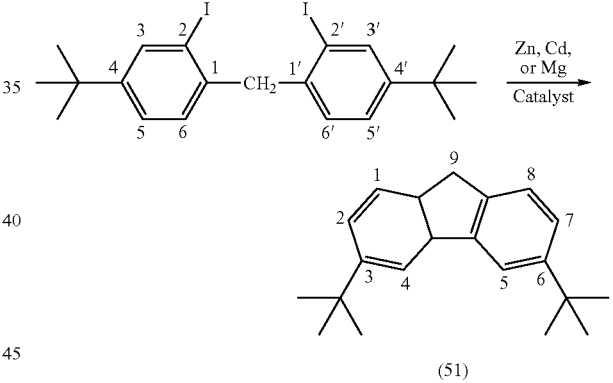

(51)

Twelve replications of reaction (51) were carried out under the reaction conditions and with the fluorene yields as set forth in Table I. N,N-dimethylformamide was used as a solvent.

TABLE I

| Replication # | 2,2'-Diiodo-4,4'-di-t-butyldiphenyl-ethane (mg) | Coupling reagent (mg) | Catalyst (mg) | Reaction time, hs | Reaction temperature, ° C. | Fluorene yield, % |
|---|---|---|---|---|---|---|
| 1 | 409 | Zn (125) | Ni(Ph₃P)₂Cl₂ (50) | 20 | 75 | 25.8 |
| 2 | 409 | Zn (125) | Ni(Ph₃P)₂Cl₂ (50) | 40 | 75 | 32.9 |
| 3 | 409 | Zn (125) | Ni[Ph₂P(CH₂)₂PPh₂)]Cl₂ (10) | 20 | 75 | 40.3 |
| 4 | 409 | Zn (125) | Ni[Ph₂P(CH₂)₂PPh₂)]Cl₂ (10) | 48 | 75 | 57.7 |
| 5 | 409 | Zn* (125) | Ni[Ph₂P(CH₂)₂PPh₂)]Cl₂ (10) | 3 | 75 | 59.0 |
| 6 | 409 | Zn* (125) | Ni[Ph₂P(CH₂)₂PPh₂)]Cl₂ (10) | 20 | 75 | 65.1 |
| 7 | 409 | Zn* (125) | Ni[Ph₂P(CH₂)₂PPh₂)]Cl₂ (10) | 48 | 75 | 78.1 |
| 8 | 888 | Zn (250) | Ni[Ph₂P(CH₂)₃PPh₂)]Cl₂ (18) | 3 | 75 | 75.0 |

TABLE I-continued

| Replication # | 2,2'-Diiodo-4,4'-di-t-butyldiphenyl-ethane (mg) | Coupling reagent (mg) | Catalyst (mg) | Reaction time, hs | Reaction temperature, ° C. | Fluorene yield, % |
|---|---|---|---|---|---|---|
| 9 | 888 | Zn (250) | Ni[Ph$_2$P(CH$_2$)$_3$PPh$_2$)]Cl$_2$ (18) | 20 | 75 | 81.2 |
| 10 | 888 | Zn (250) | Ni[Ph$_2$P(CH$_2$)$_3$PPh$_2$)]Cl$_2$ (18) | 48 | 75 | 96.2 |
| 11 | 409 | Zn (125 mg) | Pd(Ph$_3$P)$_4$ (20) | 20 | 75 | 8.1 |
| 12 | 409 | Cd (250) | Ni[Ph$_2$P(CH$_2$)$_3$PPh$_2$)]Cl$_2$ (10) | 3 | 75 | 65.0 |

*activated zinc (zinc powder was treated with 10% HCl, washed with water, EtOH and dried)

EXAMPLE 2

Synthesis of 2,7-dimethyl-3,6-di-tert-butyl-fluorene

The same procedures as in Example 1, replications 1–10 were repeated except that the reaction was carried out with 2,2'-diiodo-4,4'-di-t-butyl-5,5'-dimethyl-diphenylmethane in accordance with the following reaction:

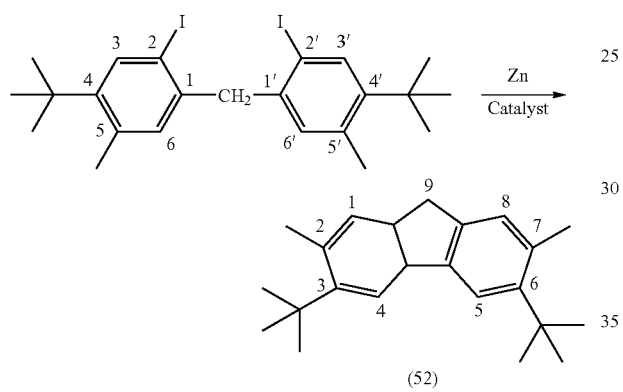

(52)

The results in terms of yield of the fluorenyl compound were roughly equivalent to those of Example 1.

EXAMPLE 3

Synthesis of 3-tert-butyl-fluorene

The same procedures as in Example 1, replications 1–10 were repeated except that the reaction was carried out with 2,2'-diiodo-4-t-butyl-diphenylmethane in accordance with the following reaction:

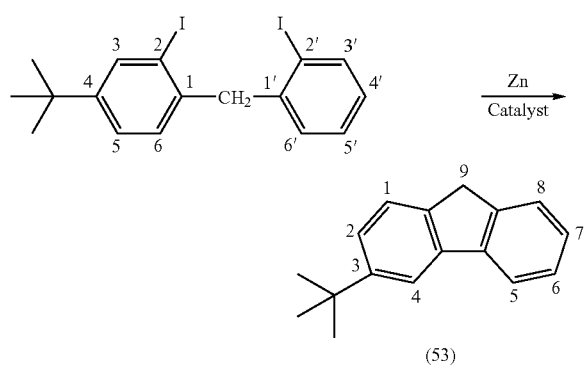

(53)

The results in terms of yield of the fluorenyl compound were roughly equivalent to those of Example 1.

EXAMPLE 4

Synthesis of 2,7-dimethyl-3,6-di-tert-butyl-fluorene a) Bromination of 3,6-di-t-butyl-fluorene To a solution of 3,6-di-t-butylfluorene (2.10 g, 7.55 mmol) in propylene carbonate (60 ml) was added NBS (2.70 g). The reaction mixture was stirred for 6 hours at 70–75° C. The mixture was then poured into water, and the precipitated solid was filtered, washed with water and dried to yield 2.71 g at a purity of 82%. $^1$H NMR (CDCl$_3$): δ 7.80 and 7.72 (each s, 2H, 1,8- and 4,5-H (Flu), 3.74 (s, 2H, H9), 1.59 (s, 18H, t-Bu).

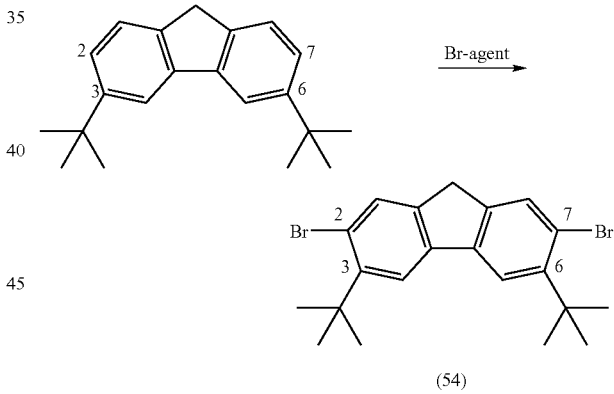

(54)

b) Coupling reaction of 2,7-dibromo-3,6-di-t-butyl-fluorene with Zn-Grignard reagent To a solution of ZnCl$_2$ (545 mg, 4.00 mmol) in THF (20 ml) was added MeMgBr (1.3 ml, 3M in Et$_2$O, 4.90 mmol). A mixture of 2,7-dibromo-3,6-di-t-butyl-fluorene (0.65 g, 1.50 mmol) and 1,2-bis(diphenyl phosphine)ethane nickel dichloride (0.110 g, 0.20 mmol) in THF (10 ml) was added to the prepared MeZnBr solution. The mixture was stirred at 25° C. for 6 hours. The reaction mixture was quenched with water, extracted with ether, dried over MgSO$_4$, and evaporated under vacuum to produce a residue which was purified by column chromatography (silica gel, hexane/CH$_2$Cl$_2$=5/1) to give 2,7-dimethyl-3,6-di-t-butyl-fluorene at a yield of 10%.

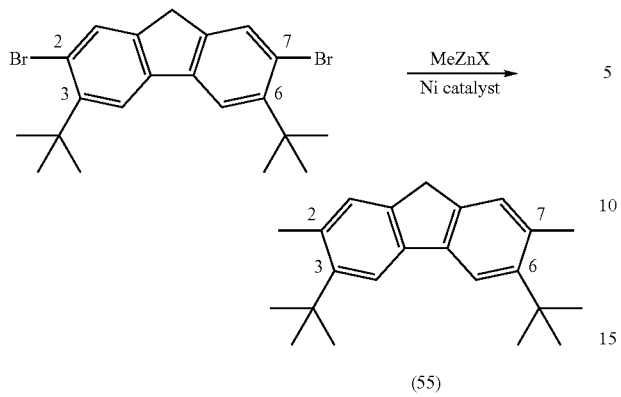

(55)

EXAMPLE 5

Synthesis of 2,7-diphenyl-3,6-di-tert-butyl-fluorene a) Bromination of 3,6-di-t-butyl-fluorene The bromination of 3,6-di-t-butyl-fluorene was carried out following the procedure of Example 4a in accordance with reaction (54).

b) 2,7-Diphenyl-3,6-di-t-butyl-fluorene

To a mixture of 2,7-dibromo-3,6-di-t-butylfluorene (0.96 g, 2.20 mmol) and Pd(PPh$_3$)$_4$ (260 mg, 0.22 mmol) in toluene (50 ml) was added a solution of phenylboronic acid (0.81 g, 6.63 mmol) in EtOH (10 ml) and a solution of Na$_2$CO$_3$ (1.5 g) in water (10 ml). The reaction mixture was stirred for 6 hours under reflux. The reaction mixture was quenched with water, extracted with ether, dried over MgSO$_4$, and evaporated under vacuum to produce a residue which was purified by column chromatography (silica gel, hexane/CH$_2$Cl$_2$=5/1) to yield 2,7-diphenyl-3,6-di-t-butyl-fluorene (0.85 g, 90%). $^1$H NMR (CDCl$_3$): δ 7.96 and 7.15 (each s, 2H, 1,8- and 4,5-H (Flu), 7.33 (m, 10H, Ph), 3.77 (s, 2H, H9), 1.27 (s, 18H, t-Bu).

(56)

EXAMPLE 6

Synthesis of 2-methyl-3,6-di-tert-butyl-fluorene a) Chloromethylation of 3,6-di-t-butyl fluorene To a solution of 3,6-di-t-buthyl fluorene (2.00 g, 7.19 mmol) and chloromethyl methyl ether (2.5 ml) in CS$_2$ (15 ml) was added at 0° C. a solution of TiCl$_4$ (0.4 ml) in CS$_2$ (5 ml). The reaction mixture was stirred for 3 hours at room temperature. The mixture was poured into ice water and extracted with ether. The ether extract was dried over sodium sulfate and evaporated under vacuum to leave a residue, which was purified by column chromatography (hexane/CH$_2$Cl$_2$=10/1) and crystallization from hot heptanes. 2-Chloromethyl-3,6-di-t-butylfluorene (Yield 0.75 g) $^1$H NMR (CDCl$_3$): δ 7.80 and 7.78 (each d, 1H, 4,5-H), 7.47 (d, 1H, J=8.1 Hz, H8), 7.34 (dd, 1H, J=8.1 Hz, J=1.5 Hz, H7), 7.31 (d, 1H, 1H, J=1.5 Hz, H1), 4.72 (s, 2H, CH$_2$Cl), 3.87 (s, 2H, H9), 1.41 (s, 18H, t-Bu). 2,7-Dichloromethyl-3,6-di-t-butylfluorene (Yield 0.63 g) $^1$H NMR (CDCl$_3$): δ 7.87 (br s, 2H, 4,5H), 7.34 (br s, 2H, 1,8-H), 4.75 (s, 4H, CH$_2$Cl), 3.95 (s, 2H, H9), 1.42 (s, 18H, t-Bu).

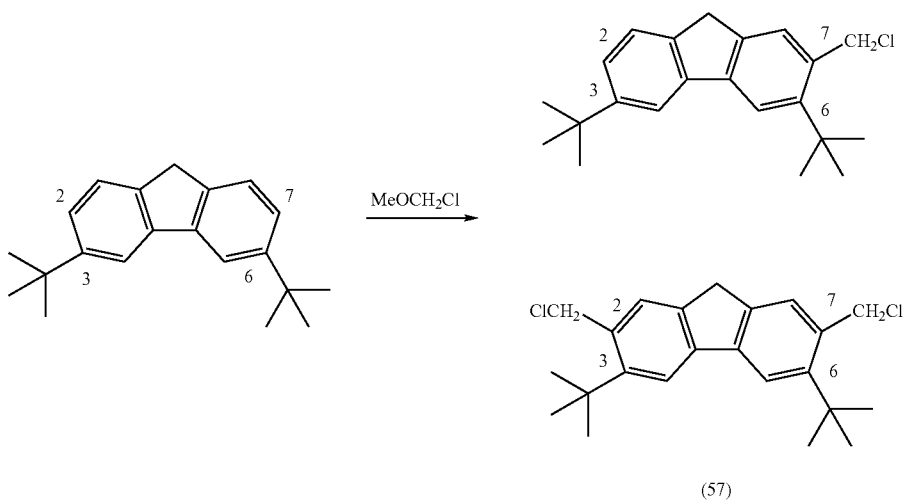

(57)

b) Reduction of 2-chloromethyl-3,6-di-t-butylfluorene

To a solution of 2-chloromethyl-3,6-di-t-butylfluorene (0.74 g, 2.26 mmol) in THF (15 ml) was added a small portion of LiAlH$_4$ (129 mg, 3.39 mmol) under stirring and the mixture was refluxed for 5 hours. The reaction was quenched with water and NaOH and extracted with ether. The ether solution was evaporated under vacuum to give a white solid yield of 0.68 g. $^1$H NMR (CDCl$_3$): δ 7.80 and 7.66 (each d, 1H, 4,5-H), 7.45 (d, 1H, J=8.1 Hz, H8), 7.31 (dd, 1H, J=8.1 Hz, J=1.5 Hz, H7), 7.14 (br s, 1H, 1H, H1), 3.69 (s, 2H, H9), 2.40 (s, 3H, Me), 1.41 (s, 18H, t-Bu).

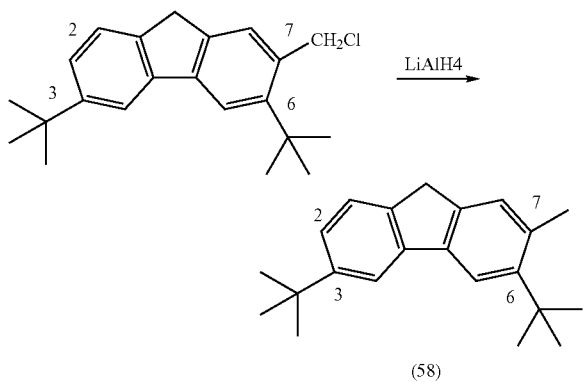

(58)

EXAMPLE 7

Synthesis of 2,7-dimethyl-3,6-di-tert-butyl-fluorene a) Chloromethylation of 3,6-di-t-butyl fluorene The same procedure as in Example 6a was repeated.

b) Reduction of 2,7-di-chloromethyl-3,6-di-t-butylfluorene

To a solution of 2,7-dichloromethyl-3,6-di-t-butylfluorene (0.75 g, 2.0 mmol) in THF (15 ml) was added a small portion of LiAlH$_4$ (220 mg, 5.8 mmol) under stirring and the mixture was refluxed for 4 hours. The reaction was quenched with water and NaOH and extracted with ether. The ether solution was evaporated under vacuum to give a white solid of 2,7-di-methyl-3,6-di-tert-butyl-fluorene with a yield of 85%.

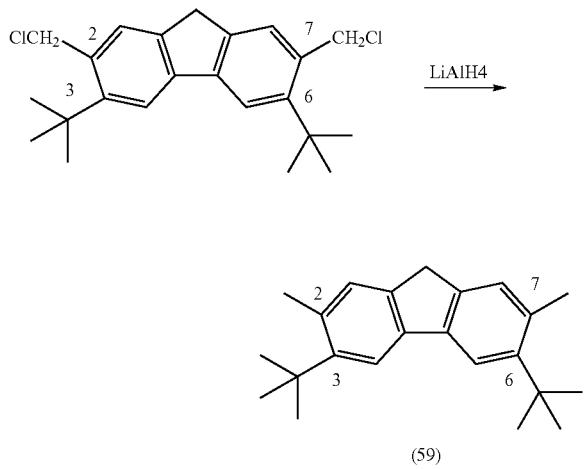

(59)

EXAMPLE 8

Synthesis of 2,4,7-tri-methyl-3,6-di-tert-butyl-fluorene

The same procedure as in Example 6 was repeated except the chloroalkylation reaction was run for 24 hours to provide a yield of 10%.

Having described specific embodiments of the present invention, it will be understood that modifications thereof may be suggested to those skilled in the art, and it is intended to cover all such modifications as fall within the scope of the appended claims.

The invention claimed is:

1. A method for the preparation of a fluorenyl-type ligand structure comprising:
    (a) providing a 2,2'-dihalogen-diphenylmethylene having a methylene bridge connecting a pair of phenyl groups, each having a halogen on a proximal carbon atom of said phenyl groups relative to the methylene bridge; and
    (b) reacting said halogenated diphenylmethylene with a coupling agent comprising a transition metal selected from Groups 2 or 12 of the Periodic Table of Elements in the presence of a nickel or palladium-based catalyst to remove the halogen atoms from the proximal carbon atoms of said phenyl groups and couple said phenyl groups at said proximal carbon atoms to produce a fluorene ligand structure.

2. The method of claim 1 wherein said coupling agent is a transition metal selected from the group consisting of zinc, cadmium and magnesium.

3. The method of claim 1 wherein said coupling agent is zinc.

4. The method of claim 1 wherein said catalyst is a monophosphine nickel complex characterized by the formula:

NiX$_2$ 2(PR$_3$)

wherein:
    R is an alkyl group, an aryl group or a alicyclic group and X is a halogen, or a diphosphine nickel complex characterized by the formula:

NiX$_2$[PR$_2$—(CH$_2$)$_n$—PR$_2$]

wherein:
    X is a halogen, R is an alkyl or aryl group and n is a number within the range of 1–10 or a palladium complex characterized by the formula:

Pd(PR$_3$)$_4$ wherein:
    R is an alkyl, an aryl or a alicyclic group.

5. The method of claim 1 wherein said halogenated diphenyl methylene is an unsubstituted ligand structure.

6. The method of claim 1 wherein said halogenated diphenylmethylene is monosubstituted with an alkyl group, an alicyclic group, or an aryl group having from 1 to 20 carbon atoms.

7. The method of claim 6 wherein said halogenated diphenylmethylene is monosubstituted with a tertiary butyl group.

8. The method of claim 1 wherein said halogenated diphenylmethylene is a dialkyl diphenylmethylene having alkyl substituents at the directly distal positions of the phenyl groups relative to said methylene bridge to produce a 3,6-dialkyl fluorene as a result of said coupling reaction.

9. The method of claim 8 wherein each of said alkyl substituents has a molecular weight of at least 43.

10. The method of claim 9 wherein said alkyl substituents are tertiary butyl groups.

11. The method of claim 1 wherein said halogenated diphenylmethylene is a substituted diphenylmethylene characterized by the formula:

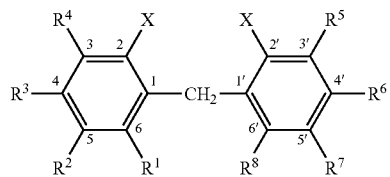

wherein:

X is a halogen atom, each $R^1$, $R^2$, $R^3$, $R^4$, $R^5$, $R^6$, $R^7$ and $R^8$ is a hydrogen atom, an aryl group, or an alkyl group, which may be the same or different, provided that no more than 3 of the $R^1$–$R^4$ groups and no more than 3 of the $R^5$–$R^8$ groups are hydrogen atoms.

12. The method of claim 11 wherein $R^1$, $R^4$, $R^5$ and $R^8$ are hydrogen and $R^2$, $R^3$, $R^6$ and $R^7$ are alkyl groups.

13. The method of claim 12 wherein $R^3$ and $R^6$ are tertiary butyl groups and $R^2$ and $R^7$ are $C_1$–$C_{20}$ alkyl groups.

14. The method of claim 11 wherein $R^3$ and $R^6$ are tertiary butyl groups aid $R^1$, $R^2$, $R^4$, $R^5$, $R^7$ and $R^8$ are hydrogen atoms.

15. The method of claim 1 wherein the reaction of subparagraph (b) is carried out at a temperature of less than 100° C.

16. The method of claim 15 wherein said temperature is within the range of 20–80° C.

17. The method of claim 16 wherein the reaction of subparagraph (b) is carried out for a time within the range of 2–3 hours.

* * * * *